US008398695B2

(12) United States Patent
Chalekian

(10) Patent No.: US 8,398,695 B2
(45) Date of Patent: Mar. 19, 2013

(54) SIDE BRANCH STENTING SYSTEM USING A MAIN VESSEL CONSTRAINING SIDE BRANCH ACCESS BALLOON AND SIDE BRANCHING STENT

(75) Inventor: Aaron Chalekian, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1634 days.

(21) Appl. No.: 11/592,691

(22) Filed: Nov. 3, 2006

(65) Prior Publication Data

US 2008/0109062 A1    May 8, 2008

(51) Int. Cl.
*A61F 2/06*    (2006.01)
(52) U.S. Cl. ...................... 623/1.11; 606/192
(58) Field of Classification Search ............... 623/1.11, 623/1.12, 1.15, 1.16, 1.2, 1.35; 606/191, 606/192, 194, 195, 198; 604/96.01, 97.01, 604/103.07, 101.01, 101.02, 101.05
See application file for complete search history.

(56) References Cited

U.S. PATENT DOCUMENTS

| 388,510 | A | 8/1888 | Terrell |
| 550,238 | A | 11/1895 | Allen, Jr. |
| 4,338,942 | A | 7/1982 | Fogarty |
| 4,490,421 | A | 12/1984 | Levy ........................... 428/35 |
| 4,546,759 | A | 10/1985 | Solar |
| 4,581,017 | A | 4/1986 | Sahota |
| 4,744,366 | A | 5/1988 | Jang |
| 4,763,654 | A | 8/1988 | Jang |
| 4,906,244 | A | 3/1990 | Pinchuk et al. ............ 606/194 |
| 4,950,239 | A | 8/1990 | Gahara et al. ............... 604/96 |
| 4,958,634 | A | 9/1990 | Jang |
| 4,994,033 | A | 2/1991 | Shockey et al. |
| 5,002,532 | A | 3/1991 | Gaiser et al. |
| 5,019,042 | A | 5/1991 | Sahota |
| 5,250,069 | A | 10/1993 | Nobuyoshi et al. ......... 606/192 |
| 5,264,260 | A | 11/1993 | Saab ............................ 428/35.5 |
| 5,270,086 | A | 12/1993 | Hamlin ........................ 428/35.2 |

(Continued)

FOREIGN PATENT DOCUMENTS

| EP | 1512381 | 3/2005 |
| WO | 97/17101 | 5/1997 |

(Continued)

OTHER PUBLICATIONS

U.S. Appl. No. 11/592,365, filed Nov. 3, 2006, Chalekian.

(Continued)

*Primary Examiner* — Ryan Severson
*Assistant Examiner* — David Eastwood
(74) *Attorney, Agent, or Firm* — Vidas, Arrett & Steinkraus, P.A.

(57) ABSTRACT

A side branch stenting system using a catheter/stent assembly having a balloon with adjacent globular and cylindrical portions and a stent mounted thereon over the cylindrical portion The stent has finger-like projections mounted over portion of the globular portion of the balloon. At a bifurcation site with another stent in place in the main vessel and having an opening into a side branch, the catheter/stent assembly is placed in the side branch and inflated. The cylindrical portion of the balloon expands the main stent body in the side vessel. The globular portion of the balloon inflates in the main vessel, constraining the main vessel and bending the finger-like projections around the circumference of the opening into the side branch.

10 Claims, 5 Drawing Sheets

U.S. PATENT DOCUMENTS

| | | | |
|---|---|---|---|
| 5,273,536 A | 12/1993 | Savas | |
| 5,304,135 A | 4/1994 | Shonk | |
| 5,308,323 A | 5/1994 | Sogawa et al. | |
| 5,328,468 A | 7/1994 | Kaneko et al. | 604/96 |
| 5,344,400 A | 9/1994 | Kaneko et al. | 604/96 |
| 5,415,635 A | 5/1995 | Bagaoisan et al. | |
| 5,500,180 A | 3/1996 | Anderson et al. | 264/532 |
| 5,536,252 A | 7/1996 | Imran et al. | |
| 5,556,383 A | 9/1996 | Wang et al. | 604/96 |
| 5,632,762 A * | 5/1997 | Myler | 606/194 |
| 5,749,890 A | 5/1998 | Shaknovich | |
| 5,797,877 A | 8/1998 | Hamilton et al. | 604/96 |
| 5,833,657 A | 11/1998 | Reinhardt et al. | 604/96 |
| 5,865,801 A | 2/1999 | Houser | |
| 5,868,777 A * | 2/1999 | Lam | 606/194 |
| 5,922,021 A | 7/1999 | Jang | |
| 6,022,359 A | 2/2000 | Frantzen | |
| 6,086,548 A | 7/2000 | Chaisson et al. | |
| 6,123,721 A | 9/2000 | Jang | |
| 6,146,356 A | 11/2000 | Wang et al. | 604/96 |
| 6,210,429 B1 | 4/2001 | Vardi et al. | |
| 6,235,053 B1 | 5/2001 | Jang | |
| 6,261,319 B1 | 7/2001 | Kveen et al. | |
| 6,270,522 B1 | 8/2001 | Simhambhatla et al. | 623/1.11 |
| 6,334,870 B1 | 1/2002 | Ehr et al. | |
| 6,348,065 B1 | 2/2002 | Brown et al. | |
| 6,471,720 B1 | 10/2002 | Ehr et al. | |
| 6,478,816 B1 | 11/2002 | Kveen et al. | |
| 6,488,653 B1 | 12/2002 | Lombardo | |
| 6,524,302 B2 | 2/2003 | Kelley | |
| 6,527,739 B1 | 3/2003 | Bigus et al. | |
| 6,582,396 B1 | 6/2003 | Parodi | |
| 6,746,479 B2 | 6/2004 | Ehr et al. | |
| 6,776,771 B2 | 8/2004 | van Moorlegem et al. | |
| 6,818,014 B2 | 11/2004 | Brown et al. | |
| 6,835,203 B1 * | 12/2004 | Vardi et al. | 623/1.34 |
| 6,905,490 B2 | 6/2005 | Parodi | |
| 6,966,889 B2 | 11/2005 | Saab | |
| 2002/0116047 A1 * | 8/2002 | Vardi et al. | 623/1.11 |
| 2002/0165521 A1 | 11/2002 | Cioanta et al. | |
| 2002/0173840 A1 | 11/2002 | Brucker et al. | |
| 2002/0193873 A1 | 12/2002 | Brucker et al. | |
| 2003/0097169 A1 | 5/2003 | Brucker et al. | |
| 2003/0109909 A1 | 6/2003 | Ledesma et al. | |
| 2003/0195606 A1 * | 10/2003 | Davidson et al. | 623/1.11 |
| 2004/0054362 A1 | 3/2004 | Lopath et al. | |
| 2004/0088007 A1 | 5/2004 | Eidenschink | |
| 2004/0138732 A1 | 7/2004 | Suhr et al. | |
| 2004/0147811 A1 | 7/2004 | Diederich et al. | |
| 2004/0172121 A1 | 9/2004 | Eidenschink et al. | |
| 2005/0015108 A1 | 1/2005 | Williams et al. | |
| 2005/0075662 A1 | 4/2005 | Pedersen et al. | |
| 2005/0119731 A1 | 6/2005 | Brucker et al. | |
| 2005/0149161 A1 | 7/2005 | Eidenschink et al. | |
| 2005/0154442 A1 | 7/2005 | Eidenschink et al. | |
| 2005/0177221 A1 | 8/2005 | Mustapha | 623/1.11 |
| 2005/0192656 A1 | 9/2005 | Eidenschink | |
| 2005/0234499 A1 | 10/2005 | Olson et al. | |
| 2005/0261722 A1 | 11/2005 | Crocker et al. | |
| 2006/0064064 A1 | 3/2006 | Jang | |
| 2006/0116748 A1 | 6/2006 | Kaplan et al. | 623/1.11 |
| 2006/0265041 A1 * | 11/2006 | Sanati et al. | 623/1.11 |
| 2006/0287712 A1 | 12/2006 | Eidenschink | |
| 2007/0038283 A1 * | 2/2007 | Mustapha | 623/1.11 |
| 2007/0050016 A1 * | 3/2007 | Gregorich et al. | 623/1.35 |
| 2007/0067011 A1 * | 3/2007 | Krolik et al. | 623/1.11 |
| 2007/0208411 A1 * | 9/2007 | Meyer et al. | 623/1.15 |
| 2008/0109056 A1 | 5/2008 | Chalekian | |

FOREIGN PATENT DOCUMENTS

| | | |
|---|---|---|
| WO | 99/36015 | 7/1999 |
| WO | 2005/041810 | 5/2005 |
| WO | 2005/084745 | 9/2005 |
| WO | WO 2006/085304 | 8/2006 |

OTHER PUBLICATIONS

International Search Report for PCT/US07/19836, which claims priority to the present application.

International Search Report for PCT/US07/19837, which claims priority to U.S. Appl. No. 11/592,365.

* cited by examiner

SIDE BRANCH STENTING SYSTEM USING A MAIN VESSEL CONSTRAINING SIDE BRANCH ACCESS BALLOON AND SIDE BRANCHING STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Stents and other radially expandable endoprostheses are typically implanted transluminally and enlarged radially after being introduced percutaneously. Such endoprostheses may be implanted in a variety of body lumens or vessels such as within the vascular system, urinary tracts, bile ducts, fallopian tubes, coronary vessels, secondary vessels, etc. Some may be used to reinforce body vessels and/or to prevent restenosis following angioplasty in the vascular system. They may be self-expanding, expanded by an internal radial force, such as when mounted on a balloon, or a combination of self-expanding and balloon expandable (hybrid expandable).

Within the vasculature it is not uncommon for stenoses to form at a vessel bifurcation. A bifurcation is an area of the vasculature or other portion of the body where a first component vessel divides into two or more component vessels. Where a stenotic lesion or lesions form at such a bifurcation, the lesion(s) can affect one, two or all three of the involved vessels.

Many of the devices that have been disclosed for deployment at bifurcations are deployed as a first stent, extending from one component vessel into a second, crossing the vessel opening ("ostium") into the third vessel. After the first stent has been deployed, an opening in the stent side-wall disposed at the ostium can then be enlarged by placing a balloon therethrough and expanding the balloon. This opening enlargement facilitates fluid flow into or from the third vessel. If needed, a second stent may also be placed in the third vessel.

In some instances of stent placement at a bifurcation a first stent configuration is employed which has a specialized side-branch opening through which the opening into the third vessel may be provided. Often such designs include a portion of the first stent which is displaced into and against the side-wall of the third vessel for a short distance beyond the ostium.

BRIEF SUMMARY OF THE INVENTION

The invention of the present application pertains, in various aspects, to methods of deploying stent assemblies at bifurcations, to catheter/stent assemblies and to two-stent assemblies useful for placement at bifurcation sites.

In one aspect the invention pertains to a method for deploying a stent assembly at a bifurcation comprising first, second and third vessels, a main channel between the first and second vessels and an ostium into the third vessel, the method comprising:

deploying a first stent in said main-channel between the first and second vessels to engage the vessel walls thereof and cross the ostium with a side branch projection extending through the ostium into the third vessel, providing a second stent which overlaps and extends beyond the side branch projection of the first stent in the third vessel, the second stent having a plurality of finger-like projections extending into the main-channel, expanding the second stent to engage the vessel wall of the third vessel, and bending said finger-like projections of the second stent around the perimeter of the ostium to engage the first stent in the main channel and provide for a linked assembly of the two stents.

In another aspect the present invention is directed to an assembly comprising:

a catheter shaft, a balloon mounted on the catheter shaft, the balloon having an inflatable first chamber having a globular configuration with a maximum perpendicular dimension (D1) taken in a plane perpendicular to the longitudinal axis of the balloon and an axial length (D3) which is not more than about 20% greater than the maximum perpendicular dimension (D1), and an independently inflatable adjacent second chamber having a generally cylindrical body portion which has a diameter (D2) which is less than the first chamber diameter axial length (D3).

a stent mounted on the catheter, the stent having a tubular body which includes a main body portion, and a plurality of finger-like projections, the stent mounted over the balloon such that the finger like projections are disposed over a portion of the first chamber and the main body portion is disposed over the second chamber.

In another aspect the present invention is directed to an assembly comprising:

a first stent having a longitudinal axis, a tubular wall and a side branch projection extending at an angle to the longitudinal axis from a portion of the tubular wall, and a catheter assembly extending through the side branch projection of the first stent, the catheter assembly comprising:

a catheter shaft, a balloon mounted on the catheter shaft, the balloon having two adjacent independently inflatable chambers, a first of said chambers having a globular configuration when inflated, and a second of said chambers disposed distally of the first chamber, the second chamber having a generally cylindrical configuration, and a second stent, the second stent having a tubular body which includes a main body portion, and, a plurality of finger-like projections the second stent mounted over the balloon such that the finger like projections are disposed over a portion of the first chamber and the main body portion is disposed over the second chamber.

In still another aspect the invention pertains to a two-stent assembly comprising:

a first stent having a tubular wall with a longitudinal axis, a side branch projection extending at an angle to the longitudinal axis from a portion of the tubular wall, with an side branch opening in the tubular wall into the side branch projection, and a second stent having a longitudinal axis extending through and overlapping the side branch projection of the first stent, the second stent having a plurality of finger-like projections at one end bent around the side branch opening to engage the tubular wall of the first stent.

These and other aspects of the invention are described further in the description, figures and claims which follow.

BRIEF DESCRIPTION OF THE SEVERAL VIEWS OF THE DRAWING(S)

DETAILED DESCRIPTION OF THE INVENTION

Figure 1:
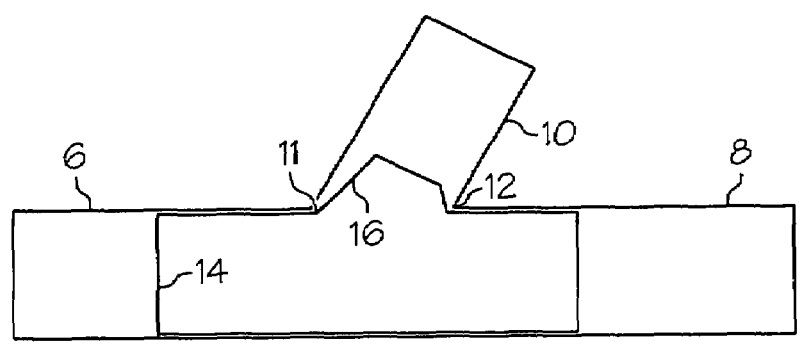
FIG. 1 is a schematic representation of a vessel bifurcation with a first stent deployed in a main channel across the bifurcation and having a side projection extending into the branch vessel.

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

For the purposes of this disclosure, like reference numerals in the figures shall be taken as referring to like features unless otherwise indicated.

FIG. 1 schematically depicts a bifurcated blood vessel having a first stent 14 disposed therein. Components of the bifurcation are first vessel 6, second vessel 8 and third vessel 10. In this particular embodiment the first and second vessels taken together form a main channel with the third vessel forming a branch vessel having an opening 11 to the main channel, but there is no particular requirement that the bifurcation form distinct main and side channels. At one side of the opening 11 (the ostium), between the vessels 8 and 10, is a carina region 12. A stent 14 is deployed at the bifurcation, extending from the first vessel into second vessel and crossing the ostium. Stent 14 includes a side branch projection 16 which extends into the third vessel 10.

Figure 6:
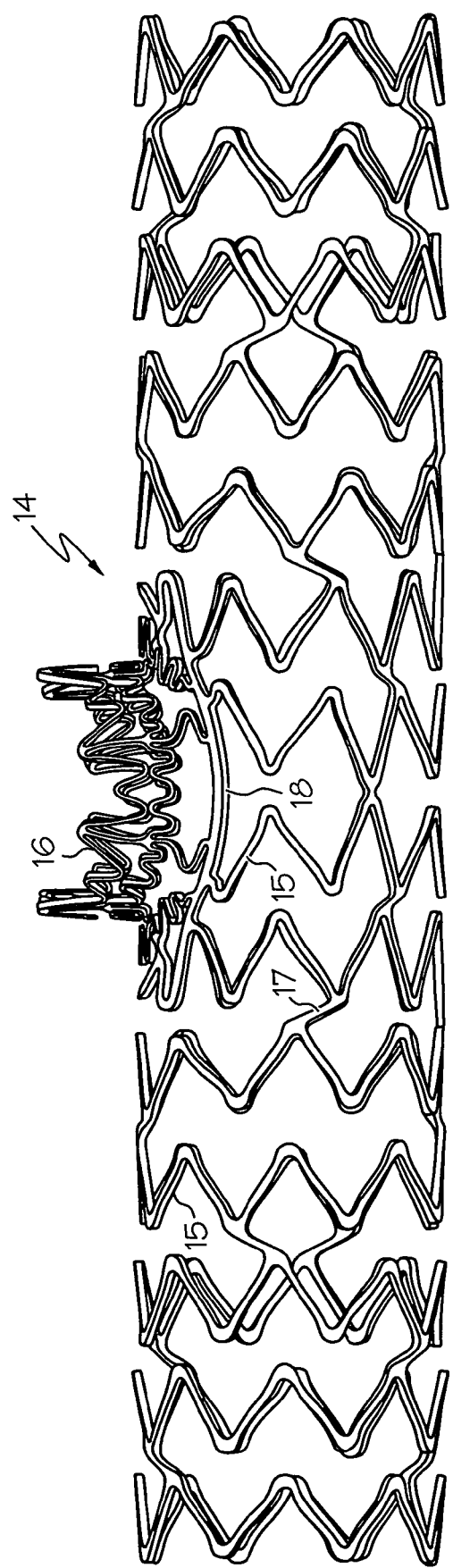
FIG. 6 is a side view of an illustrative first stent which may be employed in the invention.

Referring to FIG. 6 there is depicted an exemplary main-channel stent 14, in expanded configuration, which may be employed according to the invention. The stent 14 includes main channel support bands 15, connectors 17 between the support bands, a side channel projection 16 and a frame 18 which provides an interface between the side channel projection and the main channel support bands. Deployment of such stents may be accomplished in a known manner. Alternatively, as described in the patent application of the same inventor, U.S. application Ser. No. 11/592,365, filed Nov. 3, 2006, titled "Main Vessel Constraining Side Branch Access Balloon," incorporated herein by reference in its entirety, a multi-chamber balloon which is the same or similar to that of balloon 25, described below, may be used to extend the side channel projection 16 of stent 14 into the third vessel 10.

A first stent 14 is deployed in across an ostium in a main channel and expanded to support the main channel. The first stent has a side channel projection 16 which can be extended into the side vessel 10 after placement of the stent in the first vessel. For purposes of the present invention partial projection of the side channel projection 16 may be carried out, as shown in FIG. 1, before moving to the step illustrated in FIG. 2. This may be done in a known manner. In other embodiments, projection of the side branch portion may be complete, i.e., with the portion 16 expanded to and fully engaged with the side vessel, before moving to the next step. In still other embodiments projection of the side channel portion might be deferred until balloon expansion in the step illustrated in FIG. 3, if the portion of the first stent which forms the side channel projection has an opening which is configured in a way that allows passage of the catheter carrying the second stent directly therethrough.

Figure 2:
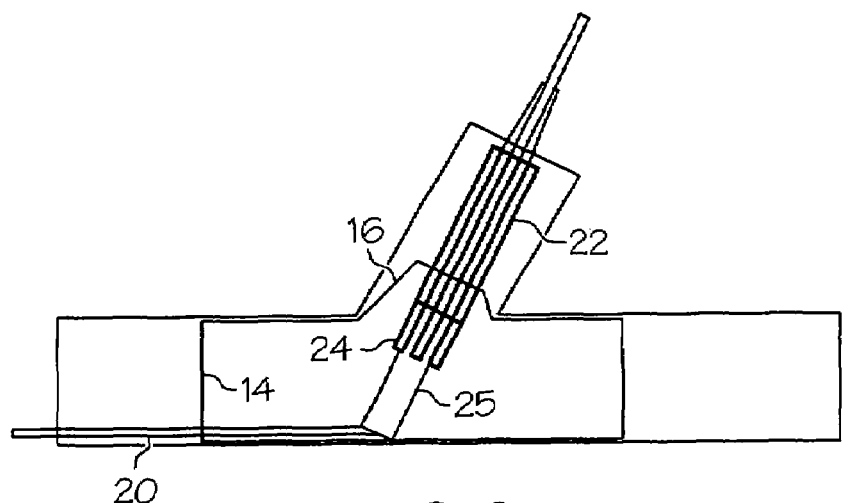
FIG. 2 is a view as in FIG. 1 with a balloon catheter and stent assembly extending through the side projection of the first stent for placement of a second stent.

Referring to FIG. 2, a catheter 20 having a second stent 22 mounted thereon over an inflatable balloon 25 is passed into the stent 14 and through the side channel projection 16, or through an opening that is enlargable and projectable to form such a side channel projection. Second stent 22 includes finger-like proximal end projections 24 that remain in the main channel.

Figure 5:
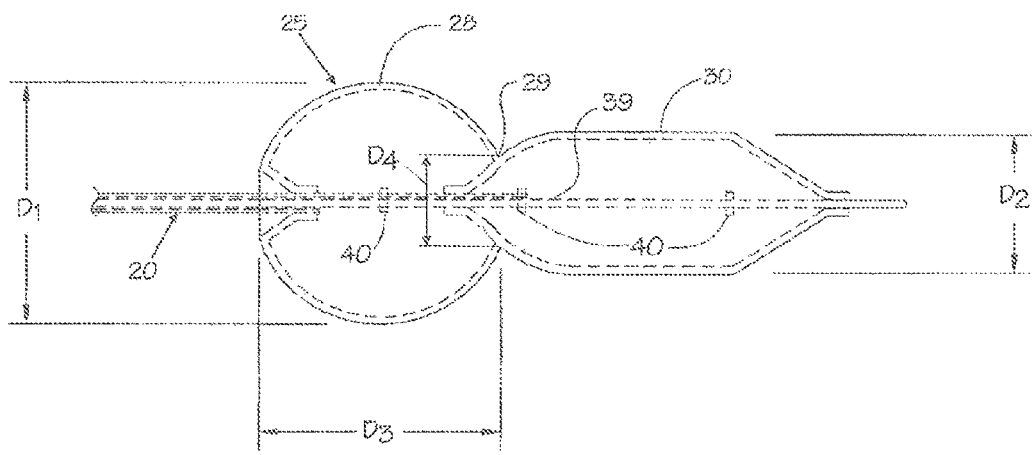
FIG. 5 is a side view of the distal end of a balloon catheter which may be employed in the invention, with the balloon inflated.

The fully inflated configuration of an exemplary configuration for a balloon 25 is depicted in FIG. 5. Balloon 25, has two chambers 28, 30. The proximal balloon portion 28 has a globular shape, for instance it may be spherical or generally spherical. The distal balloon portion 30 has a generally cylindrical configuration. The chambers 28 and 30 are independently inflatable. Separate lumens, not shown, and a lumen control, also not shown, are provided to the respective chambers so that sequenced inflation of the chambers 28 and 30 may be provided. In some embodiments it may also be desirable that the chambers 28 and 30 be concurrently inflatable at different pressures. This can be accomplished using combination of valves and pressure controls which allows for one chamber to be inflated and isolated at pressure before the other chamber is inflated.

In at least some embodiments the portions 28 and 30 are sized relative to each other such that a maximum perpendicular dimension D1 taken in a plane perpendicular to the axis of the balloon, is larger than the dimension D2, corresponding to the diameter of the cylindrical portion 30, and larger than the major dimension of the ostium of the branch opening across which the stent is to be placed. D3, the axial length of the globular portion 28, may be somewhat less than D1 due to truncation at one or both ends of the globular portion 28 along the balloon axis, but is suitably at least slightly larger than the diameter of the first stent after vessel placement and also larger than the diameter D2 of the cylindrical portion 30.

Truncation of the axial length of portion 28 occurs at least on its distal end at the junction with cylindrical portion 30. The balloon portion 28 at its proximal end is preferably, but not necessarily, mounted on the catheter in everted fashion to facilitate the angular bending of the catheter into the side arm, and in some cases this may produce some truncation of the axial length D2 of portion 28 relative to the dimension D1.

In some embodiments the junction 29 between balloon portions 28 and 30 is necked so that the dimension D4 is less than D2. If the frame 18 of stent 14 has major and minor dimensions when deployed suitably D4 is at least smaller than the major dimension of the frame 18. In some embodiments D4 is also less than the minor dimension. This sizing assures that the globular portion, when inflated in the main channel, will engage and support the frame 18.

The catheter 20 may have an inner shaft 39 that extends through both balloon portions to provide a guide wire lumen. In an alternative embodiment the catheter 20 upon which the balloon of the invention is mounted may be a fixed wire catheter or other type of catheter that is capable of being advanced through the vasculature or other body lumen(s). Radiopaque markers 40 may be provided to facilitate fluoroscopic location of the catheter in processing. In some embodiments such markers may be provided along the inner shaft within the globular portion 28 of the balloon 25, for instance near the longitudinal center thereof, and within the cylindrical portion, for instance near the ends of the cylindrical portion 30. Other locations may be marked in addition or in alternative to these locations.

Figure 7:
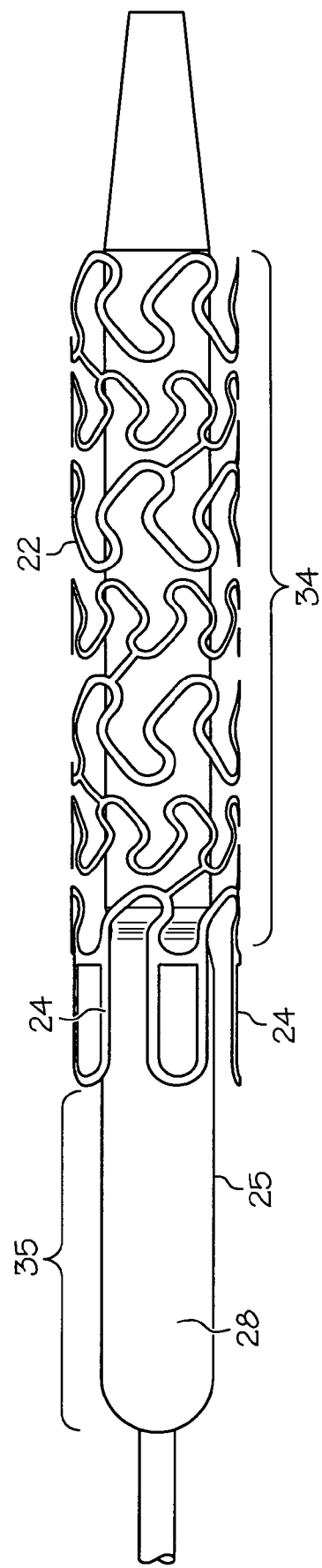
FIG. 7 is a side view of a view of the distal end of a balloon catheter which may be employed in the invention, with the balloon deflated and a second stent mounted thereon.

Referring to FIG. 7, a catheter assembly for placement of the second stent 22 is shown. The second stent 22 is mounted on the catheter assembly over the deflated balloon 25. Stent 22 has a main body portion 34, at least the substantial majority of which is mounted over the distal cylindrical balloon portion 30 and finger-like projections 24 at the proximal end which are mounted over a distal portion of globular portion 28 of the balloon. A proximal region 35 of globular balloon portion 30 is uncovered by the stent. In some embodiments the uncovered region 35 is about 50% or more of the longitudinal length of portion 30, for instance about 60 to about 85% of the length of portion 30 is not covered by the stent.

Figure 3:
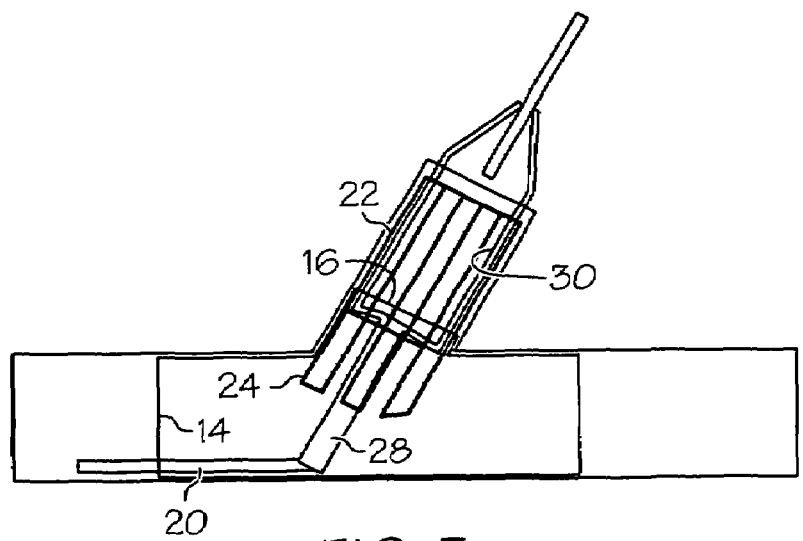
FIG. 3 is a view as in FIG. 2, showing a first inflation stage of the balloon catheter that carries the second stent.

In a first inflation stage of the inventive method, depicted schematically in FIG. 3, the cylindrical portion 30 of the balloon 26 is inflated expanding the main body of the side branch stent 24 in the vessel 10. If the side projection 16 of the first stent 14 has not been fully engaged with the vessel 10, this step will also further enlarge the side projection so that it is fully engaged with the vessel 10. At this stage the finger-like projections 24 of the second stent 22 remain extended within the main channel.

Figure 4:
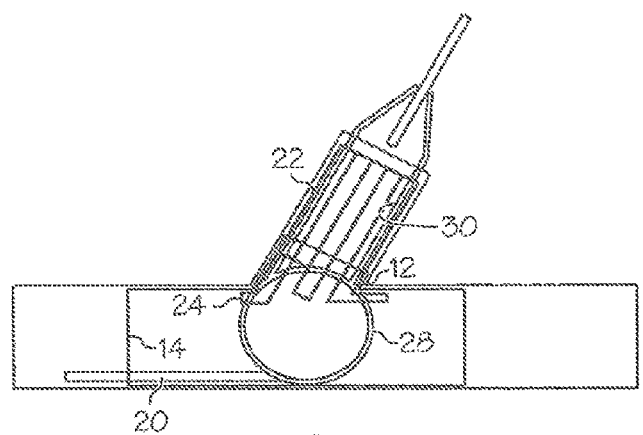
FIG. 4 is view as in FIG. 3 with the balloon fully inflated.

Then, in a second inflation stage, depicted in FIG. 4, the globular portion 28 of the balloon 25 is also inflated, filling the main channel in a region larger than the ostium between the main and side channels so that the ostium is supported, including in the carina region 12, while the finger-like projections 24 of stent 22 are bent against the wall of stent 14 around the perimeter of the frame 18. Overlap of the finger-like projections from the side branch stent 24 in the main channel, coupled with the use of a side branch projection of the stent 14 assures a secure deployment of both stents.

Except for the finger-like projections on the proximally mounted end, the second stent employed in the inventive process may have a conventional configuration. Exemplary stent configurations which may be modified to include such finger-like projections include those sold by Boston Scientific Corporation under the trademarks Liberté, TAXUS Express2, and Barracuda.

Figure 8:
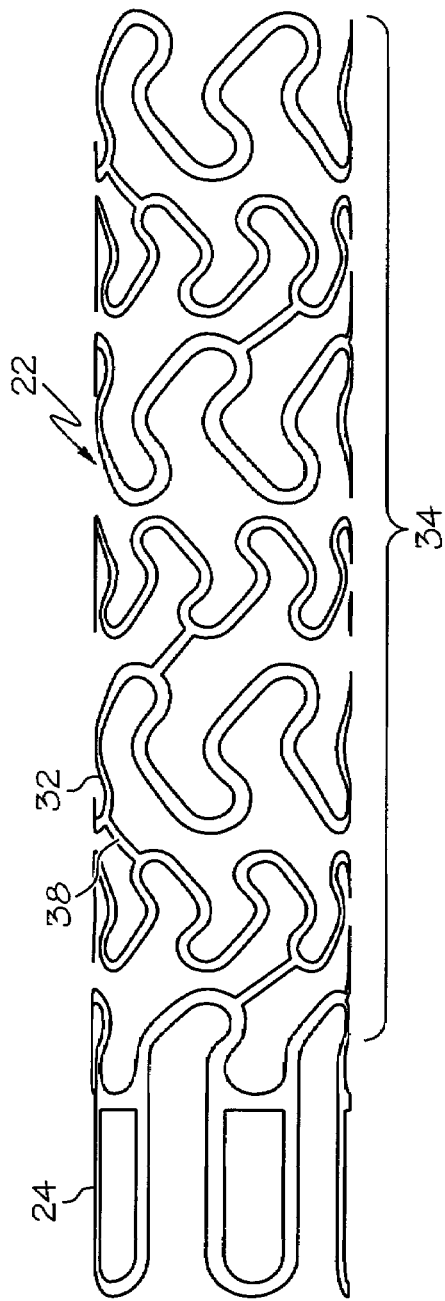
FIG. 8 is a side view of one configuration of a second stent according to the invention.
Figure 9:
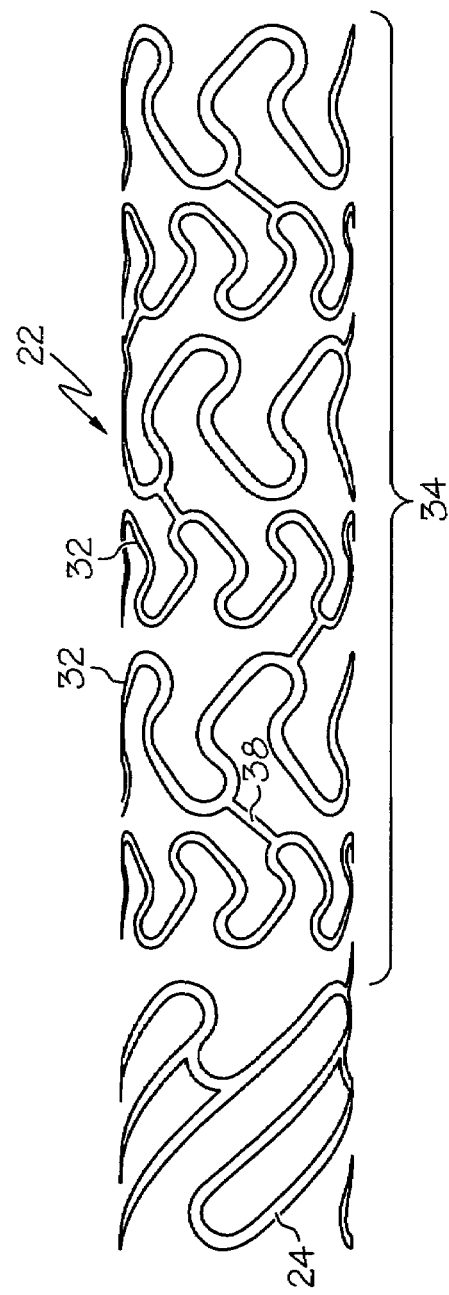
FIG. 9 is a side view of an alternate configuration of a second stent according to the invention.

FIGS. 8 and 9 are illustrative of second stents 22 which may be employed in the invention. In both figures the main body portion 34 includes annular support bands 32 and connectors 38. In FIG. 8 the finger-like portions at the end extend straight relative to the longitudinal axis of the stent. In FIG. 9 the finger-like portions extend at an angle relative to the longitudinal axis.

Referring again to FIG. 5, exemplary balloon dimensions may be taken at a nominal inflation pressure, suitably about 2 to about 6 atm, for instance 4 atm. Without limitation, D2 may be from about 1 mm to about 20 mm. In some embodiments D1 may be for instance from 10-50% larger than D2. D4 may be for instance 2-20% less than D2.

In the embodiment of the balloon 25 shown in the figures the globular portion 28 of the balloon 25 is substantially spherical other than the truncation along the axial axis which renders the axial length D3 less than the maximum perpendicular dimension D1. In other embodiments the overall shape of the balloon may be more ellipsoid or ovoid than spherical. In such embodiments, however, the axial length suitably will not more than about 20% greater than the maximum perpendicular dimension D1 and more suitably will be equal or less than the D1 dimension. Also suitably the D3 dimension will be larger than the diameter (D2) of the cylindrical portion of such balloons. Likewise, in use, a balloon size will be selected in which the axial length D3 of the globular portion is equal to or greater than the diameter of the stent 14 as deployed. In some instances the axial length D3 is about 100-150% of the diameter of the first stent diameter in the main channel, for instance about 100-120%. This assures that when inflated the portion 28 will fill the main channel and push against the frame 18 around the circumference thereof so that the tubular main channel wall is not deflected inward as part of the deployment of the second stent.

The balloon 25 may be made of known balloon polymer materials. Examples of known materials include polyesters, polyolefins, nylons, polyurethanes and various block copolymers. Exemplary documents describing suitable materials which may be employed in the invention include: U.S. Pat. No. 4,490,421 Levy, and U.S. Pat. No. 5,264,260, Saab, which describe PET balloons; U.S. Pat. No. 4,906,244, Pinchuk et al, and U.S. Pat. No. 5,328,468, Kaneko, which describe polyamide balloons; U.S. Pat. No. 4,950,239, Gahara, and U.S. Pat. No. 5,500,180, Anderson et al which describe balloons made from polyurethanes; U.S. Pat. No. 5,556,383, Wang et al, and U.S. Pat. No. 6,146,356, Wang et al, which describe balloons made from polyether-block-amide copolymers and polyester-block-ether copolymers; U.S. Pat. No. 6,270,522, Simhambhatla, et al, describes balloons made from polyester-block-ether copolymers; U.S. Pat. No. 5,344,400, Kaneko, which describes balloons made from polyarylene sulfide; U.S. Pat. No. 5,833,657, Reinhart et al, describes balloons having a layer of polyetheretherketone. All of these balloons are produced from extruded tubing of the polymeric material by a blow-forming radial expansion process. U.S. Pat. No. 5,250,069, Nobuyoshi et al, U.S. Pat. No. 5,797,877, Hamilton et al, and U.S. Pat. No. 5,270,086, Hamlin, describe still further materials which may be used to make such balloons. Physical blends and copolymers of such materials may also be used.

The balloon may be a laminate of two or more layers of the same or different polymers or blends of polymers as described above. Moreover the two balloon portions 28 and 30 may be made of the same or different polymers, blends or laminates.

The first and second stents employed in the invention may be made from any suitable biocompatible materials including one or more polymers, one or more metals or combinations of polymer(s) and metal(s). Examples of suitable materials include biodegradable materials that are also biocompatible. Suitable biodegradable materials include polylactic acid, polyglycolic acid (PGA), collagen or other connective proteins or natural materials, polycaprolactone, hylauronic acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol. At least a portion of one or both stents may be provided with material or thickness that enhances the radiopacity of the stent.

One or both of the first and second stents employed in the invention may carry one or more therapeutic agents which may be drugs or other pharmaceutical products for release at the site of deployment. The therapeutic agent may be, for instance, an anti-thrombogenic agent, vascular cell growth promoter, growth factor inhibitors, antibiotics, DNA, RNA, proteins, polysaccharides, heparin, dexamethasone, Paclitaxel, Zotarolimus, Sirolimus (i.e. rapamycin), Everolimus, phosphorylcholine, 17beta-estradiol, curcumin, malononitrilamide (e.g. malononitrilamide FK778), statins (e.g. fluvastatin), eptifibatide, irinotecan, triclosan, integrin-binding cyclic Arg-Gly-Asp peptide, cytochalasin D, mitoxantrone, carvedilol, alpha-1-antitrypsin (AAT), methotrexate, methylprednisolone, controlled release nitrogen oxide donor, tumor necrosis factor-alpha antibody, ciprofloxacin, Argatroban, angiopeptin, etc. The therapeutic agent may be carried in a coating, for instance a polystyrene-polyisobutylene-polystyrene triblock copolymer (SIBS), polyethylene oxide, silicone rubber and/or any other suitable coating material or it may be embedded or otherwise entrained in the stent structure.

The stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the stent employed in the invention.

In embodiments where the assembly comprises one or more therapeutic agents, an agent or agents on one part of the stent assembly may be similar or different to the agent or agents which may be present on other parts. The dosage of the agents on a two-stent stent assembly may vary or be different on different portions of the assembly.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. An assembly comprising:
   a first stent having a longitudinal axis, a tubular wall and a side branch opening, and
   a catheter assembly extending through the side branch projection of the first stent, the catheter assembly comprising:
   a catheter shaft,
   a balloon mounted on the catheter shaft, the balloon having two adjacent independently inflatable chambers, the balloon having a proximal balloon portion that defines a first of said chambers having a globular configuration when inflated, and a distal balloon portion that defines a second of said chambers disposed distally of the first chamber, the second chamber having a generally cylindrical configuration, and
   a second stent, the second stent having a tubular body which includes a main body portion, and, a plurality of finger-like projections the second stent mounted over the balloon such that the finger like projections are disposed over a portion of the first chamber and the main body portion is disposed over the second chamber,
   wherein the side branch opening in the first stent includes a tubular projection extending at an angle to the longitudinal axis from a portion of the tubular wall, the tubular projection overlapping with a portion of the second stent main body portion, and the proximal balloon portion has a proximal end attached to the catheter shaft in everted form.

2. An assembly as in claim 1 wherein the first chamber of the balloon has a maximum perpendicular dimension (D1) taken in a plane perpendicular to the longitudinal axis of the balloon and an axial length (D3) which is not more than about 20% greater than the maximum perpendicular dimension (D1).

3. An assembly as in claim 2 wherein, and the second chamber has a diameter (D2) which is less than the axial length (D3) of the first chamber.

4. An assembly as in claim 2 wherein the first chamber of the balloon has proximal and distal ends the maximum perpendicular dimension (D1) occurs at a location between the proximal and distal ends and the finger-like projections of the second stent extend over a portion of the first chamber from the distal end, but not beyond the location of the maximum perpendicular dimension.

5. An assembly as in claim 1 wherein the tubular wall of the first stent has a first stent diameter, and the first chamber of the balloon has an axial length (D3) at nominal inflation that is in the range of 100-150% of the first stent diameter.

6. An assembly as in claim 5 wherein the first chamber of the balloon has an axial length (D3) at nominal inflation that is in the range of 100-120% of the first stent diameter.

7. An assembly as in claim 1 wherein the globular configuration of the first chamber of the balloon is generally spherical.

8. An assembly as in claim 1 wherein at least the second chamber of the balloon is expanded.

9. An assembly as in claim 1 wherein the first and second chambers of the balloon are expanded.

10. An assembly as in claim 1 wherein the first stent includes a frame opening interface between the tubular wall and the side branch projection and the finger-like projections of the second stent are bent around the frame into engagement with the tubular wall of the first stent.

* * * * *